United States Patent
Westlund et al.

(10) Patent No.: US 11,305,111 B2
(45) Date of Patent: Apr. 19, 2022

(54) MEDICAL LEAD WITH PREFORMED BIAS

(71) Applicant: ZOLL RESPICARDIA, INC., Minnetonka, MN (US)

(72) Inventors: Randy W. Westlund, St. Paul, MN (US); Mark C. Lynn, St. Anthony, MN (US)

(73) Assignee: ZOLL RESPICARDIA, INC., Minnetonka, MN (US)

(*) Notice: Subject to any disclaimer, the term of this patent is extended or adjusted under 35 U.S.C. 154(b) by 154 days.

(21) Appl. No.: 16/689,294

(22) Filed: Nov. 20, 2019

(65) Prior Publication Data

US 2020/0101285 A1  Apr. 2, 2020

Related U.S. Application Data (63) Continuation of application No. 15/283,919, filed on Oct. 3, 2016, now Pat. No. 10,507,322, which is a continuation of application No. 12/571,103, filed on Sep. 30, 2009, now Pat. No. 9,468,755.

(51) Int. Cl.
*A61N 1/05* (2006.01)

(52) U.S. Cl.
CPC .......... *A61N 1/0558* (2013.01); *A61N 1/056* (2013.01); *A61N 1/057* (2013.01)

(58) Field of Classification Search
CPC ....... A61N 1/0558; A61N 1/057; A61N 1/056
See application file for complete search history.

(56) References Cited

U.S. PATENT DOCUMENTS

| | | | |
|---|---|---|---|
| 5,239,999 A | 8/1993 | Imran | |
| 5,938,694 A | 8/1999 | Jaraczewski | |
| 6,325,797 B1 | 12/2001 | Stewart | |
| 7,676,275 B1 | 3/2010 | Farazi et al. | |
| 8,103,359 B2 | 1/2012 | Reddy | |
| 9,468,755 B2 | 10/2016 | Westlund et al. | |
| 10,507,322 B2 | 12/2019 | Westlund et al. | |
| 2003/0040676 A1* | 2/2003 | Prentice ............. | A61N 1/36185 600/508 |
| 2003/0088244 A1 | 5/2003 | Swanson et al. | |
| 2007/0255379 A1 | 11/2007 | Williams et al. | |
| 2008/0183254 A1 | 7/2008 | Bly et al. | |
| 2008/0183259 A1 | 7/2008 | Bly et al. | |
| 2009/0088827 A1 | 4/2009 | Tockman et al. | |
| 2010/0036451 A1 | 2/2010 | Hoffer | |
| 2010/0063569 A1 | 3/2010 | Tockman et al. | |

FOREIGN PATENT DOCUMENTS

| | | |
|---|---|---|
| DE | 10103288 A1 | 8/2002 |
| WO | 2011066002 A2 | 6/2011 |

OTHER PUBLICATIONS

Decision of Reexamination issued Jan. 5, 2016 for corresponding Chinese Application No. 201080043585.5, filed Mar. 29, 2012.
(Continued)

*Primary Examiner* — Paula J Stice
(74) *Attorney, Agent, or Firm* — Lando & Anastasi, LLP (57) ABSTRACT

A medical electrical lead and methods of implanting medical electrical leads in lumens. Leads in accordance with the invention employ preformed biases to stabilize the lead within a lumen and to orient electrodes in a preferred orientation.

18 Claims, 6 Drawing Sheets

(56) References Cited

OTHER PUBLICATIONS

Canadian Office Action dated Dec. 19, 2016 for corresponding Canadian Application No. 2,775,677.
Chinese Office Action dated Sep. 4, 2017 for corresponding Chinese Application No. 201610182475.6, filed Mar. 28, 2016.
Canadian Office Action dated Nov. 27, 2017 for corresponding Canadian Application No. 2,775,677, filed Mar. 27, 2012.
Chinese Office Action dated Mar. 29, 2018 for corresponding Chinese Application No. 201610182475.6, filed Mar. 28, 2016.
Chinese Office Action dated Jul. 3, 2018 for corresponding Chinese Application No. 201610182475.6, filed Mar. 28, 2016.
International Search Report and Written Opinion of International Application No. PCT/US2010045993, filed Aug. 19, 2010.
Prosecution history from U.S. Appl. No. 12/571,103, filed Sep. 30, 2009 including: Notice of Allowance and Fee(s) Due dated Jul. 11, 2016; Non-Final Rejection dated Dec. 29, 2015; Final Rejection dated Jun. 24, 2015; Non-Final Rejection dated Oct. 20, 2014; Final Rejection dated Mar. 26, 2014; Non-Final Rejection dated Oct. 21, 2013; Final Rejection dated Dec. 13, 2012; Non-Final Rejection dated Apr. 24, 2012; and Requirement for Restriction/Election dated Mar. 19, 2012.
Prosecution history from U.S. Appl. No. 15/283,919, filed Oct. 3, 2016 including: Notice of Allowance and Fee(s) Due dated Aug. 19, 2019; Final Rejection dated Feb. 6, 2019; Non-Final Rejection dated Aug. 8, 2018; Final Rejection dated Dec. 28, 2017; Non-Final Rejection dated May 16, 2017; and Requirement for Restriction/Election dated Nov. 28, 2016.

\* cited by examiner

MEDICAL LEAD WITH PREFORMED BIAS

CROSS-REFERENCE TO RELATED APPLICATION(S)

This application is a Continuation Application of U.S. patent application Ser. No. 15/283,919, filed on Oct. 3, 2016 which is a continuation of U.S. Pat. No. 9,468,755, issued on Oct. 18, 2016, the disclosure of which is incorporated by reference in its entirety.

BACKGROUND

Electrical stimulation or sensing leads for providing medical therapy are being used in an increasing number of applications. Leads have been implanted in patients' hearts, along the spinal column, and in other locations to deliver appropriate therapy or sense physiologic conditions. Increasingly leads are implanted in veins, arteries, or other lumens to stimulate or sense tissue near the lumens.

The implantation of electrical leads in lumens presents opportunities because the leads can be fed into the patient's body and implanted without the surgery necessary to install nerve cuffs and other surgically implanted electrodes. Implanting leads in lumens also reduces the possibility of postsurgical trauma or damage to the tissue being stimulated or sensed. Difficulties associated with implanting leads in lumens include issues with lead migration and difficulty orienting the lead and electrodes.

Typical electrical leads have a proximal end that is connected to an electrical pulse generator or to circuitry configured to process signals sensed by electrodes on the leads. The electrodes on the leads are connected to the distal end by flexible and durable conductors, which are ultimately connected to an external or implantable medical device containing the required circuitry to detect sensed signals of to deliver stimulation therapy.

SUMMARY

In one embodiment in accordance with the invention, a medical electrical lead includes a lead body having a preformed helical bias with a coil diameter. The lead also has at least one electrode, and the ratio of the coil diameter to the length of the at least one electrode is at least 4:1. In other embodiments, this ratio is at least 5:1 or 6:1.

In another embodiment in accordance with the invention, a medical electrical lead includes a lead body having a preformed helical bias with a coil diameter. The preformed helical bias of this embodiment is a converging helical bias and the coil diameter is defined as the diameter of the smallest coil of the bias. The lead also has at least one electrode, and the ratio of the coil diameter to the length of the at least one electrode is at least 4:1. In other embodiments, this ratio is at least 5:1 or 6:1.

In another embodiment in accordance with the invention, a medical electrical lead includes a lead body having a preformed helical bias with a coil diameter. The preformed helical bias of this embodiment is a diverging helical bias and the coil diameter is defined as the diameter of the smallest coil of the bias. The lead also has at least one electrode, and the ratio of the coil diameter to the length of the at least one electrode is at least 4:1. In other embodiments, this ratio is at least 5:1 or 6:1.

In another embodiment in accordance with the invention, a medical electrical lead includes a lead body having preformed helical bias with a coil diameter. The lead of this embodiment includes a plurality of electrodes, and at least a portion of each of the plurality of electrodes is within a single quadrant of the helical bias. In another embodiment, each of the electrodes has a length such that ratio of the coil diameter to the lengths of the electrodes is at least 4:1. In other embodiments, this ratio is at least 5:1 or 6:1.

In yet another embodiment in accordance with the invention, a medical electrical lead includes a lead body having a lead body axis. There is a preformed bias in the lead body, and the bias has a bias axis. The angle between the lead body axis and the bias axis of this embodiment is greater than thirty degrees. In other embodiments, the angle between the lead body axis and the bias axis is greater than forty-five degrees.

Another embodiment in accordance with the invention is a method of implanting a lead in a lumen including the steps of inserting a lead in a lumen, the lead having a helical bias and a plurality of electrodes wherein at least a portion of each of the plurality of electrodes is within a single quadrant of the helical bias. The method also has a step of positioning the lead within the lumen so that a tissue of interest is within the quadrant as the quadrant extends outward radially.

In another embodiment, a method of implanting a lead in a lumen includes the steps of inserting a lead in a lumen, the lead having a helical bias and a plurality of electrodes wherein at least a portion of each of the plurality of electrodes is within a single quadrant of the helical bias. The method also includes a step of positioning the lead within the lumen so that a tissue of interest is within the quadrant as the quadrant extends outward radially wherein the lumen includes the right brachiocephalic vein and the tissue of interest comprises the right phrenic nerve. In other embodiments the lumen includes the left brachiocephalic vein and the tissue of interest includes the left phrenic nerve, the lumen includes the superior vena cava and the tissue of interest includes the right phrenic nerve, the lumen includes the right internal jugular vein and the tissue of interest includes the hypoglossal nerve, or the lumen comprises the junction between the right brachiocephalic vein and the right subclavian vein.

DETAILED DESCRIPTION

Figure 1:
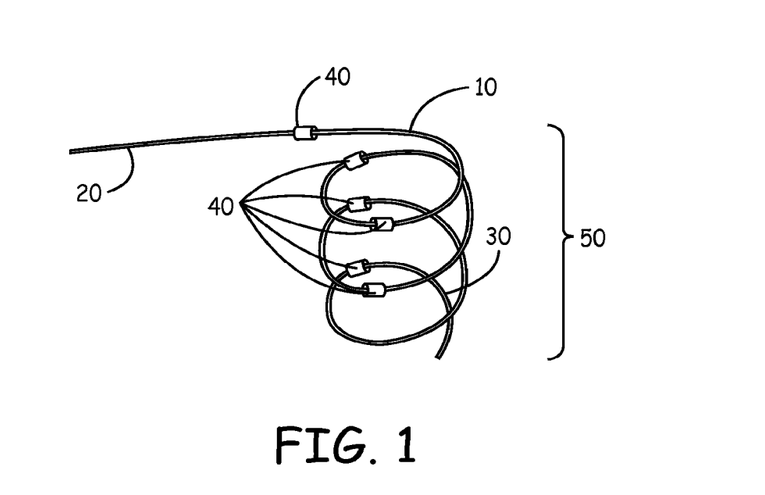
FIG. 1 is a perspective view of a lead in accordance with embodiments of the invention.

FIG. 1 is a perspective view of a lead in accordance with embodiments of the invention. The lead has a lead body 10 with a proximal portion 20 and a distal end 30. Electrodes 40 are distributed along a distal portion of the lead body 10. A bias region 50 near the distal end is formed in a helical or circular fashion. This bias region 50 may be formed by wrapping the lead around a spindle of other shape imparting structure and heat treating or otherwise shaping the lead body 10 in a way that the lead will be biased to return to this preformed shape. The lead body may be constructed from a shape memory polymer or metal or of any material suitable for the purpose. If constructed from a shape memory polymer, for example polyurethane, the thickness or diameter of the lead body or other parameters may be varied to adjust the degree of rigidity of the bias.

The bias may be helical or generally circular. The primary difference between what is described herein as a helical bias and a circular bias is the pitch of the helix. A circular bias is one in which the pitch of the helix is less than or equal to the thickness of the lead. That is the coils of the helix touch or overlap with one another when the lead is in its unstressed position. If the pitch of the helix is greater than the thickness of the lead, the bias is referred to herein as helical. For the purposes of this discussion, circular and helical biases are interchangeable unless specifically noted as the pitch is essentially the only difference.

The bias 50 shown in FIG. 1 is generally is a helix of a constant diameter. This embodiment is usable to secure a lead within a relatively large lumen. In practice, the diameter of the helix is designed to be slightly larger than the lumen in which it is implanted, and the pressure of the bias against the lumen wall retains the lead within the lumen. Once so retained, the electrodes are in a position to sense activity in nearby tissues or electrically stimulate nearby tissues.

As an example, the embodiment of FIG. 1 could be implanted within the right or left brachiocephalic vein or superior vena cava of a patient. Both the right and left brachiocephalic veins are similar in size, ranging from approximately 15 mm to 22 mm in diameter. An embodiment for this application may, for example, have a helix/coil diameter of 20 mm. The helix/coil length, measured along the axis of the helix from the first curvature to the end of the lead, may in this example be 30-40 mm.

Figure 2:
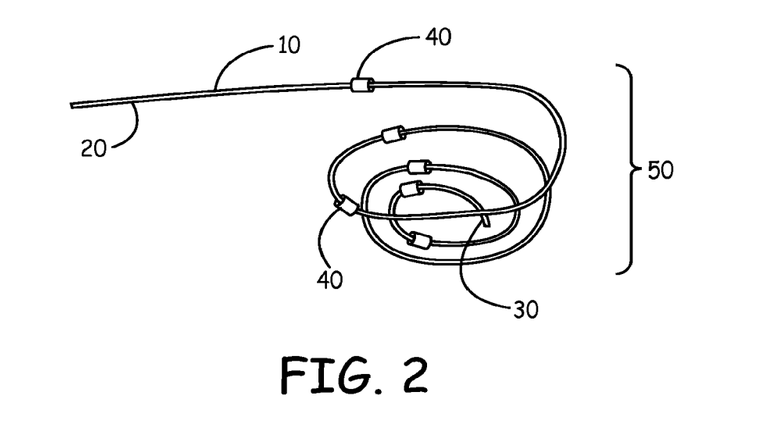
FIG. 2 is a perspective view of a lead in accordance with embodiments of the invention.

FIG. 2 is a perspective view of a lead in accordance with embodiments of the invention. Like the embodiment in FIG. 1, this embodiment has a lead body 10 with a proximal portion 20 and a distal end 30. Electrodes 40 are disposed generally distally on the lead body. A bias 50 is formed in a helical or circular fashion near the distal end. This bias 50 is formed as a converging circle or helix, with the coils having a decreasing diameter from the proximal portion 20 toward the distal end 30.

A lead in accordance with FIG. 2 could be usable to secure electrodes within lumens at a junction of two or more lumens. If a lumen or vessel diverges to form two, for example, this lead could be employed such that the larger diameter coils of the helix are deployed within the larger diameter region where the lumens diverge while the smaller diameter coils reside within the single lumen formed by the junction. In this manner, a consistent anchoring pressure may be provided in a region of diverging diameters due to a junction of lumens.

Figure 3:
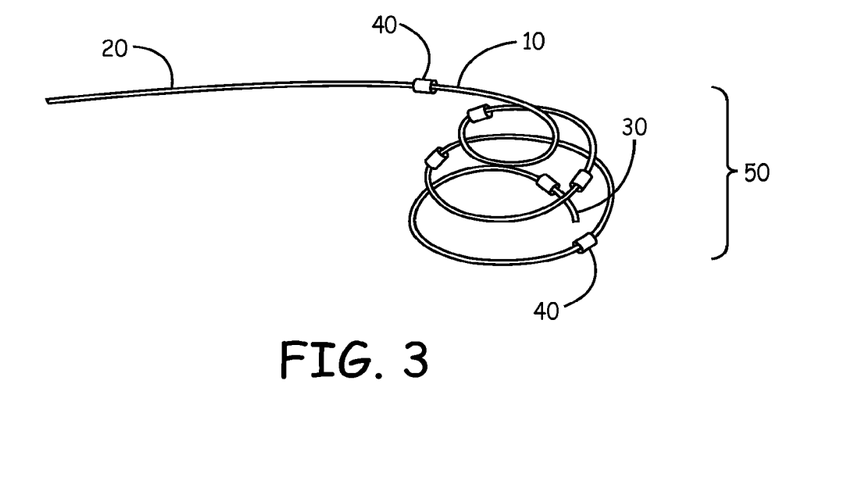
FIG. 3 is a perspective view of a lead in accordance with embodiments of the invention.

FIG. 3 is a perspective view of a lead in accordance with embodiments of the invention. The embodiment of FIG. 3 includes a lead body 10 having a proximal portion 20 and a distal end 30. One or more electrodes 40 are disposed along the lead body. A bias 50 is formed proximate the distal end 30. The bias in this embodiment has a diverging circle or helix, in which the diameter of the coils increases from the proximal portion 20 to the distal end 30. If a two lumens or vessels converge to form one, for example, this lead could be employed such that the larger diameter coils of the helix are deployed within the larger diameter region where the lumens come together while the smaller diameter coils reside within the single lumen formed by the junction. In this manner, a consistent anchoring pressure may be provided in a region of converging diameters due to a junction of lumens.

Figure 4:
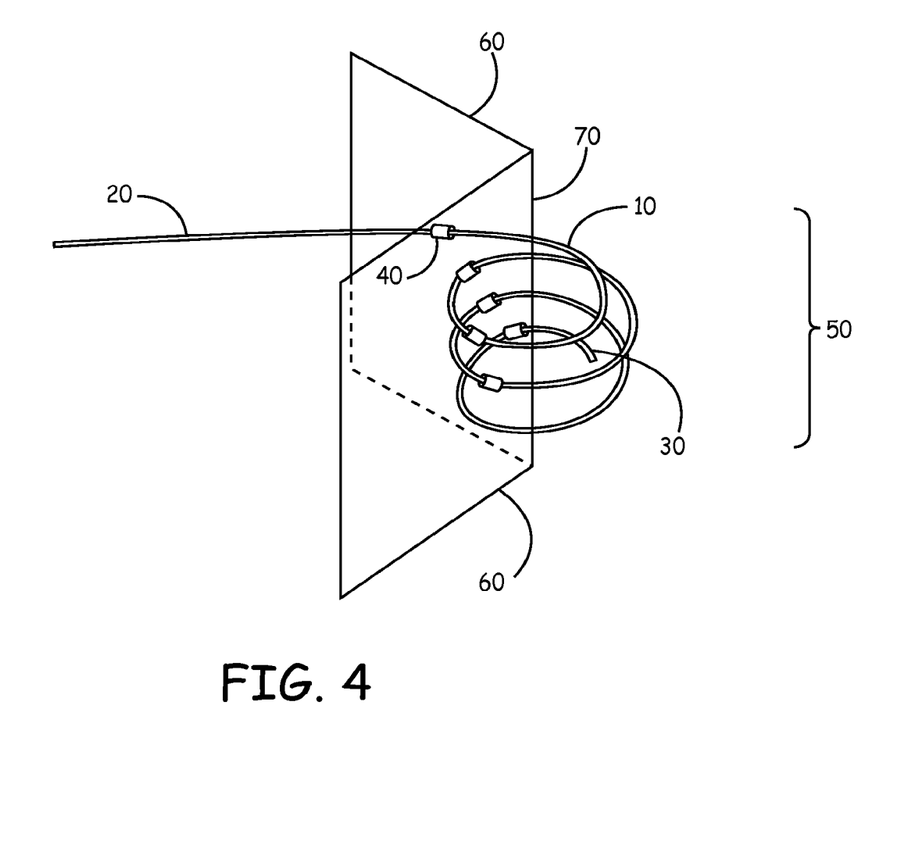
FIG. 4 is a perspective view of a lead in accordance with embodiments of the invention.

FIG. 4 is a perspective view of a lead in accordance with embodiments of the invention. The embodiment of FIG. 4 includes a lead body 10 having a proximal portion 20 and a distal end 30. A circular or helical bias 50 is proximate the distal end. Electrodes 40 are disposed along the lead body generally in one quadrant of the helical portion, as defined by illustrative planes 60. Illustrative planes 60 meet at line 70, which defines the axis of the bias 50. At least some portion of each electrode of this embodiment is in this quadrant. By distributing the electrodes in this fashion, the area to be stimulated or sensed by the electrodes upon implantation can have the maximum number of electrodes oriented nearby.

For example, if the lead of FIG. 4 were implanted in a right brachiocephalic vein with the desired effect of stimulating the right phrenic nerve or sensing nerve traffic, the quadrant of the bias 50 defined by planes 60 could be oriented along the right lateral side of the brachiocephalic vein to maximize the effectiveness of any stimulation or signal sensing provided by the electrodes 40.

Figure 5:
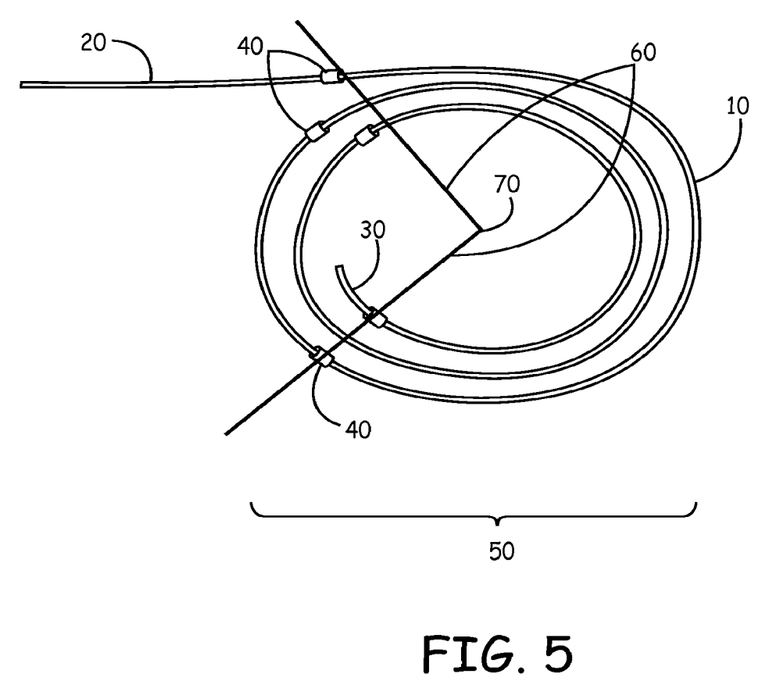
FIG. 5 is a plan view of a lead in accordance with embodiments of the invention.

FIG. 5 is a plan view of a lead in accordance with embodiments of the invention. This embodiment has a lead body 10 having a proximal portion and a distal end. A bias 50 of a circular or helical basis is proximate the distal end 30. Electrodes are 40 distributed such that at least a portion of each electrode is within a quadrant of the helix 50 as defined by illustrative planes 60. This view is of a lead as in FIG. 4, and is taken along line 70.

Implanting a lead in accordance with embodiments of the invention involves advancing the lead to the desired location with the aid of some sort of stiffening or straightening device, such as an internal wire or stylet or external guide catheter. The lead is advanced to the desired location and the stiffening device is removed, allowing the bias to revert to its imparted or natural shape. The lead position is evaluated through X-ray and standard venography techniques. The lead can be advanced or retracted as necessary, with or without the stiffening device in place. The lead can also be rotated as necessary, again, with or without the stiffening member. In fact, without the stiffening member in place, the lead can be rotated to reposition the electrodes or in some instances to "tighten" or "loosen" or "expand" the bias 50. In cases where the electrodes on the lead are arranged so that least a portion of each electrode is located within a quadrant of the bias, the lead is oriented so that the tissue of interest to be sensed or stimulated falls within an extension of that quadrant. That is, if one extends the planes 60 of FIGS. 4 and 5 radially away from line 70 while the lead is implanted, the tissue of interest would fall within the quadrant, and preferably toward the center of the quadrant.

Figure 6:
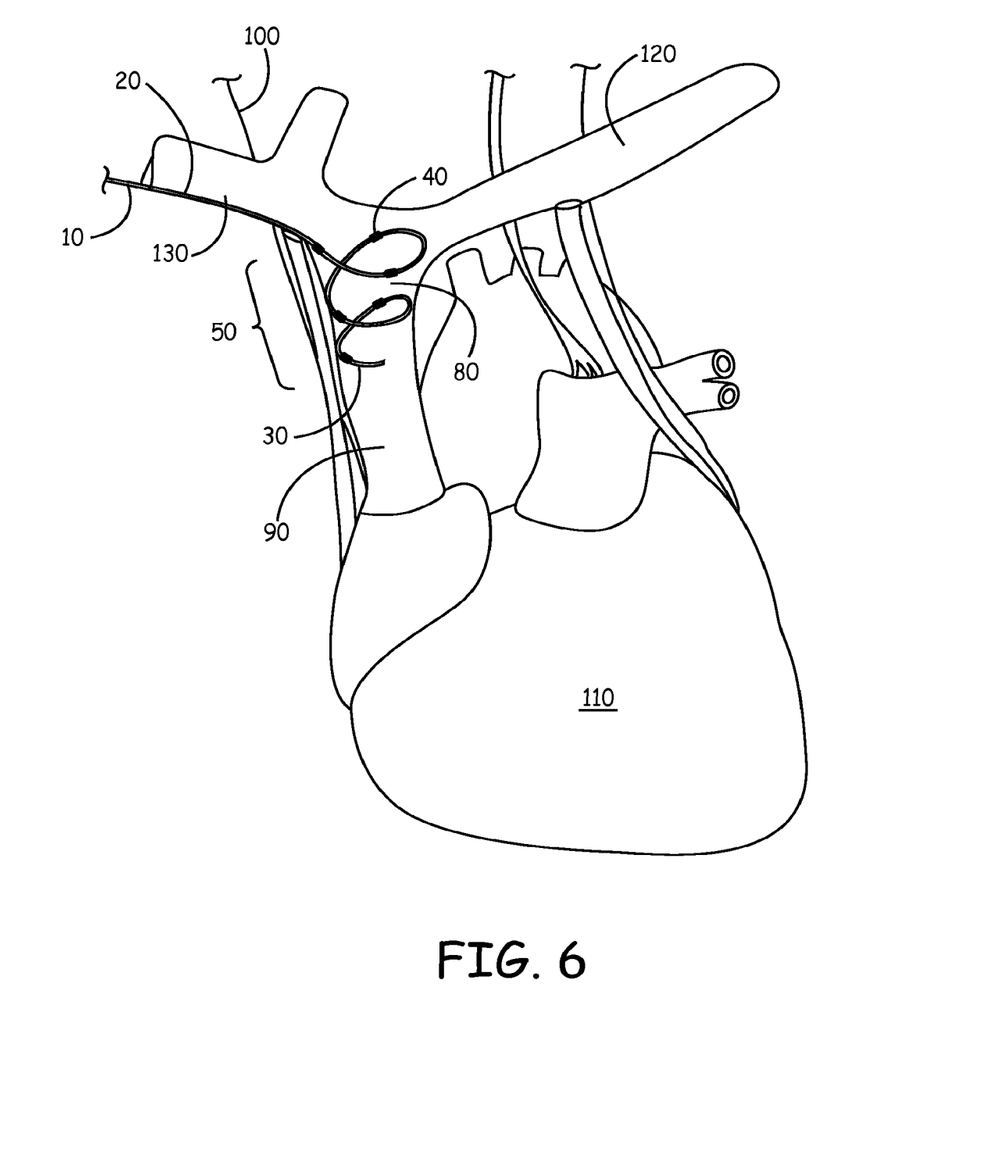
FIG. 6 is a schematic view of a lead in accordance with embodiments of the invention implanted in a patient.

FIG. 6 is a schematic view of a lead in accordance with embodiments of the invention implanted in a patient. The lead has a lead body 10 having a proximal portion 20 and a distal end 30. Electrodes 40 are disposed on the lead body, which includes a bias portion 50. The lead is disposed in the right brachiocephalic vein 80 of the patient through the subclavian vein 130 and extends into the superior vena cava 90. The transition from the right brachiocephalic to the superior vena cava is imprecise, and references to the right brachiocephalic vein within this disclosure refer to both the right brachiocephalic and superior vena cava unless otherwise indicated. The electrodes 40 are configured to stimulate, or to sense nerve activity of, the right phrenic nerve 100 of the patient. In this embodiment the bias 50 could be a consistent coil diameter, a converging coil diameter, or a diverging coil diameter.

Veins within the thorax are subject to intrathoracic pressures caused by diaphragmatic contraction. When the diaphragm contracts, it creates negative intrathoracic pressures that cause veins within the thorax to dilate, increasing venous volume and enlarging the cross sectional area of the vein. In addition there is a downward translation of the heart 110 and lungs that can stretch and elongate the superior vena cava 90 and brachiocephalic 80, 120 veins. Pulsing from the cardiac cycle also can be translated to the superior vena cava 90 and brachiocephalic 80, 120 veins. These physiologic dynamics create many challenges, which inventors have overcome in leads in accordance with embodiments of the invention.

The shape of the bias 50 of some embodiments is circular, in the helical form or in the true circular form. The circular and helical shapes exert force against the inner luminal surface of the vein creating a frictional force that retains the lead in the vein. This radial fixation force is created by forming a shape or bias in the lead that is "slightly" larger diameter than the vessel diameter. This relationship can be described in some embodiments as a bias diameter to vessel diameter ratio of between 1.1:1 and 1.3:1. The bias 50 diameter in these embodiments is slightly larger because some of the larger veins in which these embodiments are implanted are fairly malleable and the inventors have found that these veins do not significantly constrain the leads, resulting in bias orientations upon implantation that are substantially similar to the bias' unconstrained position prior to implantation. Inventors have used this knowledge to create desired biases shapes that are then implanted in much the same configuration.

The bias 50 can be formed in a constant diameter fashion, a diverging helix or circle, or a converging helix or circle. The different shapes may be more or less suitable for varying anatomy and different locations. If the lead is intended for the junction of the subclavian vein 130 and brachiocephalic vein 80, a converging helix may provide superior fixation and electrode contact. If the targeted site involves the brachiocephalic vein junction or superior vena cava the diverging helix may be superior. In each case the varying diameters of the coils may be proved more intimate contact with the vessel wall for better fixation and electrode contact. The most proximal portions of the helix (the first ½ to full revolution) may serve as a mechanism of decoupling. This feature may decouple external forces (i.e. arm, shoulder, etc. motion) from the electrodes. It may also permit the bias 50 of the lead, that part that engages the vein, to move (this motion comes from respiration, coughing, sneezing, cardiac impulse) independent from the proximal lead portion 20.

In some embodiments, the electrodes 40 are arranged within a quadrant of the bias 50 so that they are more apt to stimulate or sense the tissue of interest. In the case where the right phrenic nerve 100 is of interest, the lead may be situated so that the most proximal electrode is located in the subclavian vein and the quadrant of the bias 50 that includes the electrodes 40 is places on the right lateral portion of the right brachiocephalic 80. In cases where the electrodes on the lead are oriented so at least a portion of each electrode is within a defined quadrant, the lead could be further oriented so that the quadrant, when extended, includes a significant portion of the right phrenic nerve.

Figure 7:
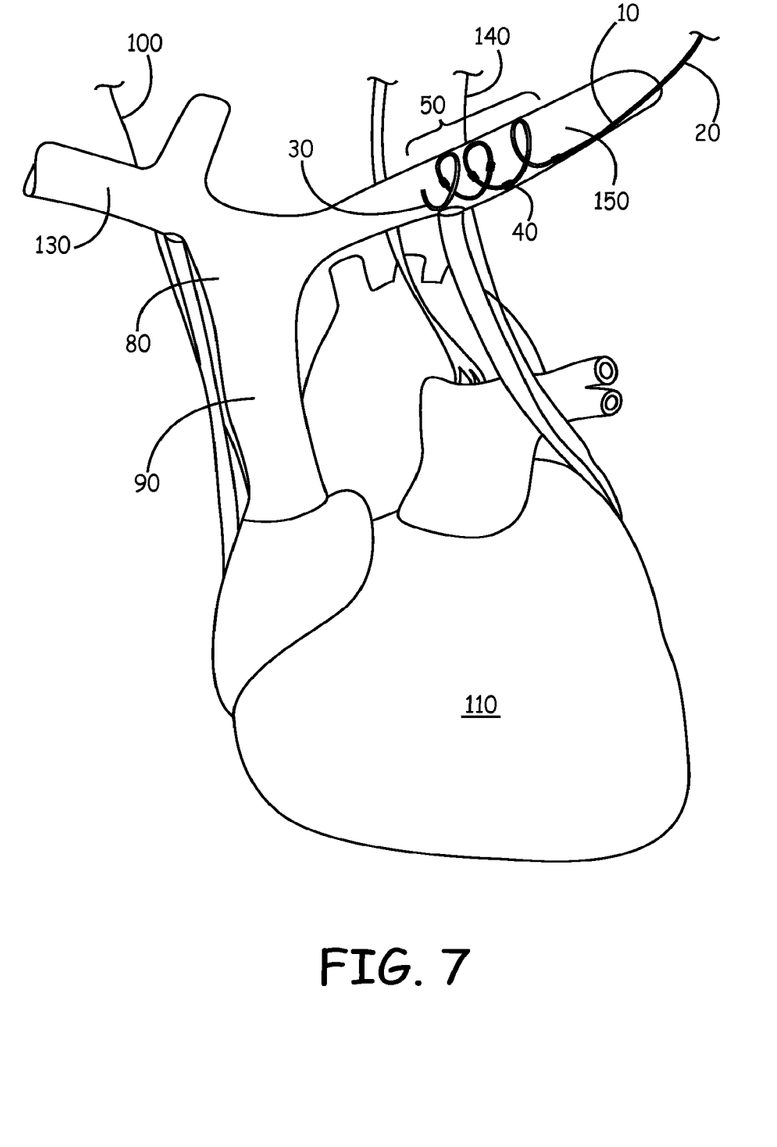
FIG. 7 is a schematic view of a lead in accordance with embodiments of the invention implanted in a patient.

FIG. 7 is a schematic view of a lead in accordance with embodiments of the invention implanted in a patient. The lead has a lead body 10 having a proximal portion 20 and a distal end 30. Electrodes 40 are disposed on the lead body, which includes a bias portion 50. The lead is disposed in the left brachiocephalic vein 150 of the patient. The electrodes 40 are configured to stimulate, or to sense nerve activity of, the left phrenic nerve 140 of the patient. In this embodiment the bias 50 could be or a consistent coil diameter, a converging coil diameter, or a diverging coil diameter.

The left phrenic nerve 140 passes behind or anterior to the left brachiocephalic vein 150 at a somewhat skew angle to the vein 150. In some embodiments the electrodes 40 may be arranged in the bias 50 so that they are in the anterior quadrant of the bias 50 as the lead is implanted. In some of these and other embodiments, the pitch of the coil of the bias 50 may be relatively more circular than helical to concentrate the electrodes more closely to where the nerve 140 passes closest to the vein 150. As discussed above, in some embodiments the bias is implanted in the lead and adopts a configuration substantially similar to that of the unstressed unimplanted lead.

Figure 8:
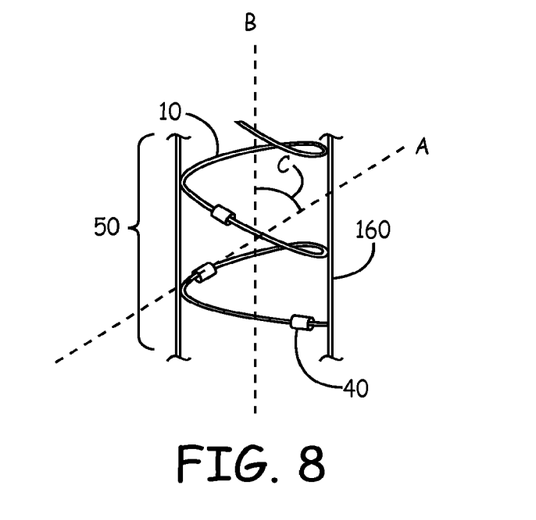
FIG. 8 is a schematic drawing of a lead in accordance with embodiments of the invention implanted in a cross section of a lumen.

FIG. 8 is a schematic drawing of a lead in accordance with embodiments of the invention implanted in a cross section of a lumen. The lead has a lead body 10 and electrodes 40 disposed thereon. The lead body 10 has a preformed bias 50 that forces at least portions of the lead body 10 against the walls 160 of a lumen. The lumen has a main axis B that is coaxial with the bias axis, also B. The lead body has a main axis A, in this case measured at an exemplary electrode. The angle C between the coil axis B and lead axis A can be generally described as skew. If the lead body 10 has an axis A more parallel to the coil axis B, the lead body 10 tends to define an elongated helix that is potentially more susceptible to motion artifact. Inventors have learned that lead bodies with their axes A perpendicular to the coil axis B define a helix with greater stability within a lumen, possibly due to a greater force applied transverse to the lumen wall 160.

The fact that the angle C is skew to a significant degree means that the lead body is traversing laterally across the lumen more so than coaxially. This means that in order for the lead 10 and electrodes 40 to be close to the lumen wall 160 for stimulation or sensing, the lead 10 and electrode 40 combination must approximate the curvature of the lumen wall.

Figure 9:
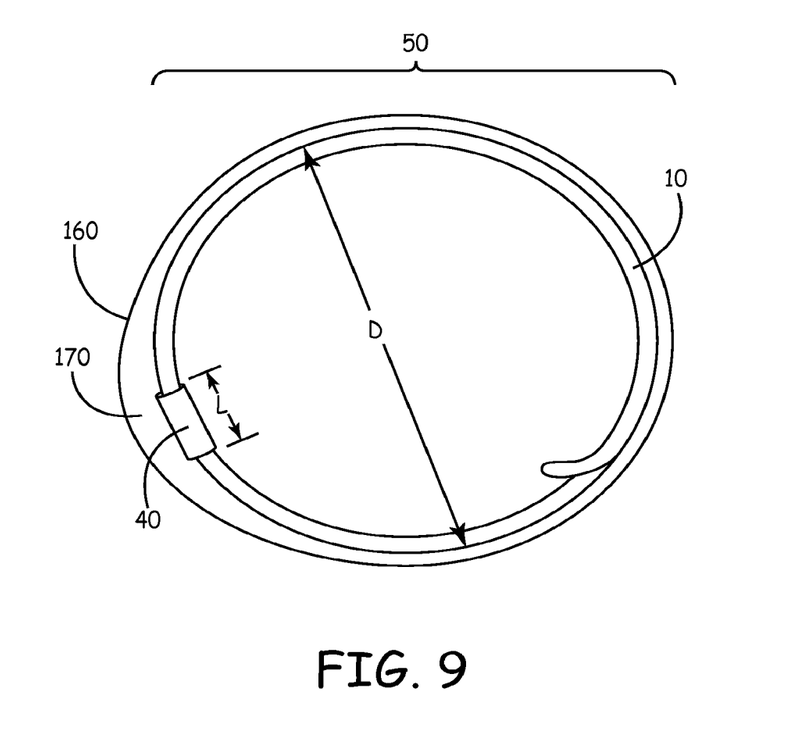
FIG. 9 is a schematic drawing of a lead in accordance with embodiments of the invention as in FIG. 8 from a view along an axis such as B.

FIG. 9 is a schematic drawing of a lead in accordance with embodiments of the invention as in FIG. 8 from a view along an axis such as B. The lead has a lead body 10 form in a circular or helical bias 50, of which one coil is shown, and an electrode 40. The coil has a diameter D and the electrode has a length L. In some embodiments, electrodes are appropriately sized in length L relative to coil diameter D. In some cases if the electrode is too long, a circular discontinuity that can separate, or push away, or prevent intimate contact of the electrode with the vessel wall is created, leading to a gap 170.

Inventors have found that for some embodiments the ratio of the length L of the electrode to the diameter D of the coils of the bias 50 can be relevant. For coils configured for implantation into vessels the size of the right or left brachiocephalic veins, for example, an effective D:L ratio may be 4:1 or greater. This ratio is particularly relevant when the main lead axis A is particularly skew to the lumen axis B as discussed with respect to FIG. 8. A sufficient L:D ratio may result in the lead body adopting a more continuous circular shape that rests against the luminal surface 160. It is conceivable that a more continuous circular shape will induce less stress, lower opportunity for lumen damage, and thus lower probability of negative tissue response at the electrode site than a shape with periodic flat areas/sections with corners. This ratio has application to both the in situ helical and circular shapes.

One skilled in the art will appreciate that the invention can be practiced with embodiments other than those disclosed. The disclosed embodiments are presented for purposes of illustration and not limitation, and the invention is limited only by the claims that follow.

What is claimed is:

1. An implantable medical electrical lead comprising:
a lead body having a preformed converging helical bias extending from a proximal portion to a distal end, wherein a coil diameter decreases from the proximal portion toward the distal end of the helical bias: and
at least one electrode disposed on a distal portion of the lead body and having a length parallel to a lead body portion on which it is disposed, wherein a ratio of a coil diameter to the length of the at least one electrode is greater than or equal to 4:1, where the coil diameter is defined as a diameter of a smallest coil of the converging helical bias.

2. The medical electrical lead of claim 1 wherein the ratio of the coil diameter to the length of the at least one electrode is greater than or equal to 5:1.

3. The medical electrical lead of claim 1, wherein the ratio of the coil diameter to the length of the at least one electrode is greater than or equal to 6:1.

4. The medical electrical lead of claim 1, wherein the at least one electrode comprises a plurality of electrodes, wherein the length of each electrode of the plurality of electrodes is at least partially located within a single quadrant of the converging helical bias.

5. The medical electrical lead of claim 4, wherein at least two of the plurality of electrodes are radially offset from each other.

6. The medical electrical lead of claim 4, wherein each of the plurality of electrodes is radially offset from the other electrodes of the plurality of electrodes.

7. The medical electrical lead of claim 1, wherein a diameter of the converging helical bias is greater than a diameter of a lumen in which it is to be disposed in a ratio of between 1.1:1 and 1.3:1.

8. An implantable medical electrical lead comprising:
a lead body having a preformed converging helical bias extending from a proximal portion to a distal end, wherein a coil diameter decreases from the proximal portion toward the distal end of the converging helical bias; and
a plurality of electrodes disposed on a distal portion of the lead body and having a length parallel to a lead body portion on which it is disposed, wherein at least a portion of each electrode of the plurality of electrodes is located within a single quadrant of the converging helical bias, wherein at least two of the plurality of electrodes are radially offset from each other; and wherein a ratio of the coil diameter to the length of at least one electrode is greater than or equal to 4:1, where the coil diameter is defined as a diameter of a smallest coil of the converging helical bias.

9. The implantable medical electrical lead of claim 8, wherein the ratio of the coil diameter to the length of the at least one electrode is greater than or equal to 5:1.

10. The implantable medical electrical lead of claim 8, wherein the ratio of the coil diameter to the length of the at least one electrode is greater than or equal to 6:1.

11. The medical electrical lead of claim 8, wherein each of the plurality of electrodes is radially offset from the other electrodes of the plurality of electrodes.

12. The medical electrical lead of claim 8, wherein a diameter of the converging helical bias is greater than a diameter of a lumen in which it is to be disposed in a ratio of between 1.1:1 and 1.3:1.

13. A method of implanting a medical electrical lead, the method comprising:
inserting a lead body in a first lumen, the lead body comprising:
a lead body having a preformed converging helical bias extending from a proximal portion to a distal end, wherein a coil diameter decreases from the proximal portion toward the distal end of the converging helical bias; and
at least one electrode disposed on a distal portion of the lead body and having a length parallel to a lead body portion on which it is disposed, wherein a ratio of the coil diameter to the length of the at least one electrode is greater than or equal to 4:1, where the coil diameter is defined as a diameter of a smallest coil of the preformed converging helical bias, wherein at least a portion of each of the at least one electrode is within a single quadrant of the preformed converging helical bias; and
positioning the lead within the first lumen at a junction of the first lumen and a second lumen, the first lumen having a first diameter and the second lumen having a second diameter that is less than the first diameter such that the proximal portion of the preformed converging helical bias places a radial fixation force on the first lumen such that the preformed converging helical bias is retained in the junction and such that a tissue of interest is within the quadrant as the quadrant extends outward radially.

14. The method of claim 13, wherein the first diameter of the first lumen corresponds to a diameter of a subclavian vein and the second diameter of the second lumen corresponds to a diameter of a right brachiocephalic vein.

15. The method of claim 14, wherein the tissue of interest corresponds to a right phrenic nerve.

16. The method of claim 13, wherein a diameter of the proximal portion of the preformed converging helical bias is greater than the first diameter of the first lumen in a ratio of between 1.1:1 and 1.3:1.

17. The method of claim 13, wherein the ratio of the coil diameter to the length of the at least one electrode is greater than or equal to 5:1.

18. The method of claim 13, wherein the ratio of the coil diameter to the length of the at least one electrode is greater than or equal to 6:1.

* * * * *